United States Patent
Heida et al.

(10) Patent No.: US 8,766,029 B2
(45) Date of Patent: Jul. 1, 2014

(54) PROCESS FOR PROVIDING A VAPOROUS PURIFIED CRUDE C4 CUT AS A FEED STEAM FOR AN EXTRACTIVE DISTILLATION WITH A SELECTIVE SOLVENT

(71) Applicant: BASF SE, Ludwigshafen (DE)

(72) Inventors: Bernd Heida, Ellerstadt (DE); Randolf Hugo, Dirmstein (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/736,446

(22) Filed: Jan. 8, 2013

(65) Prior Publication Data

US 2013/0178684 A1 Jul. 11, 2013

Related U.S. Application Data

(60) Provisional application No. 61/585,282, filed on Jan. 11, 2012.

(51) Int. Cl.
*C07C 7/00* (2006.01)

(52) U.S. Cl.
USPC .............. 585/809; 585/802; 585/810

(58) Field of Classification Search
None
See application file for complete search history.

(56) References Cited

U.S. PATENT DOCUMENTS

| | | | | |
|---|---|---|---|---|
| 3,317,627 A | * | 5/1967 | King et al. | 585/617 |
| 3,803,258 A | * | 4/1974 | Weitz et al. | 585/862 |
| 7,105,616 B2 | * | 9/2006 | Auer | 526/133 |
| 7,557,257 B2 | * | 7/2009 | Heida | 585/833 |
| 2003/0181772 A1 | * | 9/2003 | Meyer et al. | 585/324 |
| 2006/0241329 A1 | * | 10/2006 | Heida | 585/809 |
| 2008/0228019 A1 | * | 9/2008 | Heida | 585/324 |

FOREIGN PATENT DOCUMENTS

WO WO 2011/110562 A1 9/2011

OTHER PUBLICATIONS

U.S. Appl. No. 13/732,668, filed Jan. 2, 2013, Bernd Heida, et al.

* cited by examiner

*Primary Examiner* — Tam N Nguyen
(74) *Attorney, Agent, or Firm* — Oblon, Spivak, McClelland, Maier & Neustadt, L.L.P.

(57) ABSTRACT

Mixtures of hydrocarbons predominantly having 4 carbon atoms per molecule known as $C_4$ cuts are used in obtaining crude 1,3-butadiene by a thermal cracking process. Vaporous purified crude $C_4$ cuts are produced from liquid crude $C_4$ cuts, containing butanes, butenes, 1,3-butadiene, $C_3$ hydrocarbons, $C_4$ oligomers and polymers, and $C_{5+}$ hydrocarbons via an extractive distillation by fist removing the $C_4$ oligomers and polymers and the $C_{5+}$ hydrocarbons and then vaporizing the liquid crude $C_4$ cut in a vaporizer vessel. The vaporizer vessel is directly or indirectly in contact with a stripping column where liquid $C_4$ cuts are supplied to the upper region, direct gas and liquid exchange with the vaporizer vessel occurs in the lower region, and vaporous purified crude $C_4$ cuts are removed from the top region.

9 Claims, 1 Drawing Sheet

Figure 1:
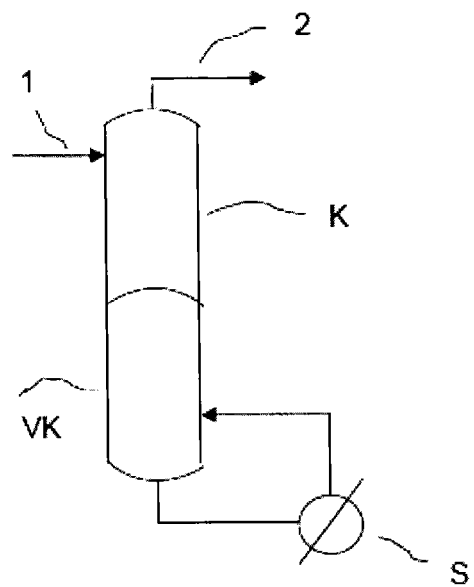

PROCESS FOR PROVIDING A VAPOROUS PURIFIED CRUDE C4 CUT AS A FEED STEAM FOR AN EXTRACTIVE DISTILLATION WITH A SELECTIVE SOLVENT

The invention relates to a process for providing a vaporous purified crude $C_4$ cut as a feed stream for an extractive distillation with a selective solvent.

The term "$C_4$ cut" refers to mixtures of hydrocarbons having predominantly 4 carbon atoms per molecule. $C_4$ cuts are obtained, for example, in the preparation of ethylene and/or propylene by thermal cracking, typically in steamcrackers, especially naphtha crackers or FCC crackers (fluid catalyzed cracking), of a petroleum fraction such as liquefied petroleum gas, light gasoline or gas oil. In addition, $C_4$ cuts are obtained in the catalytic dehydrogenation of n-butane and/or n-butene. $C_4$ cuts generally comprise butanes, butenes, 1,3-butadiene, small amounts of $C_3$- and $C_4$-acetylenes, 1,2-butadiene and $C_{5+}$ hydrocarbons.

The separation of $C_4$ cuts is a complicated distillation problem due to the small differences in the relative volatilities of the components. Therefore, the separation is performed by what is called an extractive distillation, i.e. a distillation with addition of a selective solvent (also referred to as extractant), which has a higher boiling point than the mix to be separated and which increases the differences in the relative volatilities of the components to be separated.

A multitude of processes are known for separation of $C_4$ cuts by means of extractive distillation using selective solvents. They have the common feature that countercurrent flow of the $C_4$ cut to be separated in vapor form with the liquid selective solvent under suitable thermodynamic conditions, generally at low temperatures, frequently in the range from 20 to 80° C., and at moderate pressures, frequently at standard pressure to 6 bar, results in loading of the selective solvent with the components from the $C_4$ cut for which it has a higher affinity, whereas the components for which the selective solvent has a lower affinity remain in the vapor phase and are drawn off as the top stream. Subsequently, the laden solvent stream is freed of the components in the selective solvent by fractionation under suitable thermodynamic conditions, i.e. at higher temperature and/or lower pressure compared to the first process step, in one or more further process steps.

Crude $C_4$ cuts comprise impurities which would lead to problems in the extractive distillation, more particularly formation of solvent foam and apparatus fouling, and so they have to be removed specifically before the supply of the crude $C_4$ cut to the extractive distillation, in order to ensure reliable operation of the extractive distillation.

Impurities which lead to the above problems are especially components having a higher boiling point than 1,3-butadiene, and among these particularly $C_{5+}$ hydrocarbons (predominantly hydrocarbons having 5 or more carbon atoms per molecule, isoprene, $C_4$ oligomers and polymers, i.e. oligomers and optionally polymers of butadiene having the formula $(C_4H_6)_n$, where n is greater than or equal to 2). The proportion of the $C_{5+}$ hydrocarbons in $C_4$ cuts depends particularly on the operating conditions in the thermal cracking and is up to 1000 ppm by weight or even up to 5000 ppm by weight, in specific cases up to 1% by weight, based on the total weight of the crude $C_4$ cut. The $C_4$ oligomers and polymers form especially as a result of storage and transport; the proportion thereof therefore depends predominantly on the storage and transport conditions, especially temperature, duration, degree of inertization of the atmosphere under which the storage and/or transport takes place.

In addition, $C_3$ hydrocarbons, i.e. hydrocarbons having three carbon atoms per molecule, of the extractive distillation can also lead to problems; these are especially methylacetylene, which has a similar affinity for the selective solvents typically used, such as 1,3-butadiene. The proportion of the $C_3$ hydrocarbons in the feed stream for the extractive distillation should therefore be limited to not more than 50 ppm by weight, based on the total weight of the feed stream.

The above problems in the prepurification of the feed stream for extractive distillation of crude $C_4$ cuts have to date been solved in different ways: in a known mode of operation, in a distillation column connected upstream of the extractive distillation, $C_3$ hydrocarbons are removed via the top and the other components are drawn off via the bottom. The bottom stream is subsequently supplied, for the purpose of removal of the high-boiling components compared to 1,3-butadiene, to a vaporizer vessel, i.e. to an apparatus with a single plate. In the vaporizer vessel, the crude $C_4$ stream depleted of $C_3$ components is virtually completely vaporized under flow rate control, such that the high-boiling components compared to 1,3-butadiene in the remaining liquid component do not exceed 5% by weight, especially 1% by weight, or even 0.1% by weight, based on the total weight of the crude $C_4$ cut supplied to the vaporizer vessel. The liquid stream remaining in the vaporizer vessel is discharged as a purge stream. A disadvantage here, however, is that, via the purge stream, together with the high boilers, high proportions of materials of value, $C_4$ hydrocarbons, are also discharged.

With respect to this, it is an object of the invention to provide a process by which the secondary components disruptive in the extractive distillation in crude $C_4$ cuts can be removed in a technically simple manner with low capital and energy costs, as a result of which the service life of the extractive distillation column is increased.

This object is achieved by a process for providing a vaporous purified crude $C_4$ cut as a feed stream for an extractive distillation with a selective solvent, proceeding from a liquid crude $C_4$ cut as a feed stream, comprising not only butanes, butenes and 1,3-butadiene but also $C_3$ hydrocarbons, $C_4$ oligomers and polymers, and $C_{5+}$ hydrocarbons, said purified vaporous crude $C_4$ cut comprising
    less than two thirds of the $C_{5+}$ hydrocarbons present in the feed stream and
    less than 5% by weight of the $C_4$ oligomers and polymers present in the feed stream,
comprising the process steps of
1) removing the $C_4$ oligomers and polymers and the $C_{5+}$ hydrocarbons, in each case down to the residual contents specified above for the vaporous purified crude $C_4$ cut, and
2) vaporizing the liquid crude $C_4$ cut in a vaporizer vessel, wherein
the vaporizer vessel is assigned a stripping column having one or more plates, to which the liquid $C_4$ cut is supplied in the upper region thereof, which is in direct gas and liquid exchange with the vaporizer vessel in the lower region thereof, and from which the vaporous purified crude $C_4$ cut is drawn off in the upper region thereof, the stripping column being operated without a condenser at the top of the column.

It has been found that it is possible, in a technically simple and not very energy-intensive manner, to increase the high boiler removal in the vaporizer vessel and at the same time to reduce the loss of $C_4$ hydrocarbons from the vaporizer vessel via the purge stream, by associating a stripping column with the vaporizer vessel.

It is possible in this context, more particularly for the construction of new plants, to place the stripping column atop the vaporizer vessel, i.e. to integrate vaporizer vessel and stripping column in a single apparatus.

In another embodiment, especially for existing plants, it is also possible to associate the vaporizer vessel with a stripping column, i.e. to provide vaporizer vessel and stripping column as separate apparatuses.

Vaporizer vessels are simple apparatus known in process technology. They generally comprise a vessel in which a gas phase can separate from a liquid phase, and a heat exchanger arranged within or outside the vessel.

According to the invention, a stripping column is assigned to the vaporizer vessel.

Since the stripping column and the vaporizer vessel are merely provided for depletion of high boilers, it is possible to operate the stripping column in a simple manner, without a condenser at the top of the column.

A typical crude $C_4$ cut from a naphtha cracker has the following composition in percent by weight:

| | |
|---|---|
| Propane | 0-0.5 |
| Propene | 0-0.5 |
| Propadiene | 0-0.5 |
| Propyne | 0-0.5 |
| n-Butane | 3-10 |
| i-Butane | 1-3 |
| 1-Butene | 10-20 |
| i-Butene | 10-30 |
| trans-2-Butene | 2-8 |
| cis-2-Butene | 2-6 |
| 1,3-Butadiene | 35-65 |
| 1,2-Butadiene | 0.1-1 |
| Ethylacetylene | 0.1-2 |
| Vinylacetylene | 0.1-3 |
| C5 | 0-0.5 |

Crude $C_4$ cuts from naphtha crackers thus comprise predominantly butanes, butenes and 1,3-butadiene. In addition, small amounts of other hydrocarbons are present. $C_4$-acetylenes are frequently present up to a proportion of 5% by weight or else up to 2% by weight.

For the extractive distillation defined at the outset, useful selective solvents are generally substances or mixtures having a higher boiling point than the mixture to be separated and a greater affinity for conjugated double bonds and triple bonds than for simple double bonds and single bonds, preferably dipolar and more preferably dipolar aprotic solvents. For apparatus reasons, preference is given to less corrosive or noncorrosive substances.

Suitable selective solvents for the process according to the invention are, for example, butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, especially N-methylpyrrolidone. In general, N-alkyl-substituted lower aliphatic acid amides or N-alkyl-substituted cyclic acid amides are used. Particularly advantageous are dimethylformamide, acetonitrile, furfural and especially N-methylpyrrolidone.

However, it is also possible to use mixtures of these solvents with one another, for example of N-methylpyrrolidone with acetonitrile, mixtures of these solvents with cosolvents such as water and/or tert-butyl ethers, for example methyl tert-butyl ether, ethyl tert-butyl ether, propyl tert-butyl ether, or n- or isobutyl tert-butyl ether.

N-Methylpyrrolidone is particularly suitable, preferably in aqueous solution, especially with 8 to 10% by weight of water, more preferably with 8.3% by weight of water.

In order to avoid problems in the extractive distillation, the feed stream with which the latter should be supplied is a vaporous purified crude $C_4$ cut comprising less than 50 ppm by weight of $C_3$ hydrocarbons, based on the total weight of the purified vaporous crude $C_4$ cut, less than two thirds of the $C_{5+}$ hydrocarbons present in the feed stream and less than 5% by weight of the $C_4$ oligomers and polymers present in the feed stream.

It has been found that it is possible to improve the high boiler removal in a simple manner by associating the vaporizer vessel with a stripping column.

In addition, it is possible in the process according to the invention to remove high-boiling components compared to 1,3-butadiene from the $C_4$ cut with a much lower loss of product of value, $C_4$ hydrocarbons.

Preferably, the $C_3$ hydrocarbons in the vaporous purified crude $C_4$ cut are depleted to less than 10 ppm by weight, based on the total weight of the vaporous purified crude $C_4$ cut, or else further preferably to less than 4 ppm by weight, in a distillation column connected upstream of the vaporizer vessel.

Further preferably, the $C_{5+}$ hydrocarbons in the vaporous purified crude $C_4$ cut are depleted to less than half of the $C_{5+}$ hydrocarbons present in the feed stream.

The stripping column is operated preferably at a top pressure in the range from 3 to 7 bar absolute, further preferably at a top pressure in the range from 4.5 to 5.5 bar absolute.

The stripping column especially has 1 to 15 theoretical plates.

The invention is illustrated in detail hereinafter with a drawing and by working examples.

Figure 2:
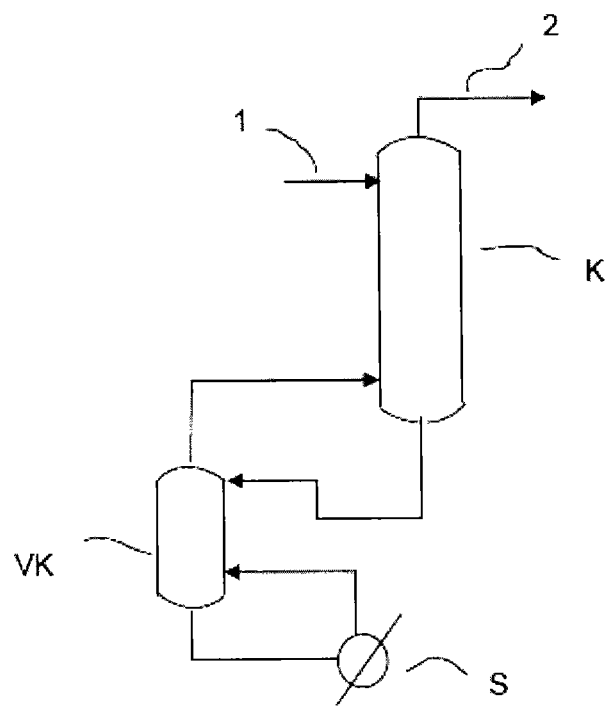

The drawings show, specifically,

FIG. 1 a schematic diagram of the vaporizer vessel with stripping column atop and FIG. 2 a schematic diagram of a vaporizer vessel with associated stripping column.

The schematic diagram in FIG. 1 shows a vaporizer vessel, VK, at the upper end of which is connected a stripping column K, in such a way that the vaporizer vessel VK and the stripping column K form a single apparatus. At the lower end of the vaporizer vessel VK, a reboiler is provided.

The stripping column K is supplied, in the upper region thereof, with the liquid crude $C_4$ cut as stream 1, and the purified crude $C_4$ cut, stream 2, is drawn off at the top of the stripping column K.

FIG. 2 shows the schematic diagram of a further preferred embodiment, in which the vaporizer vessel VK and the stripping column K are configured as separate apparatuses, and wherein direct gas and liquid exchange is provided at the upper end of the vaporizer vessel VK with the stripping column K.

The vaporizer vessel VK is equipped with a reboiler S.

The stripping column K is supplied in the upper region thereof with the liquid $C_4$ cut as stream 1, and the vaporous purified crude $C_4$ cut, stream 2, is drawn off as a top stream.

WORKING EXAMPLES

The starting material is a liquid crude $C_4$ cut as a feed stream for a 100 kt/year plant, comprising 200 ppm of propane, 400 ppm of propene, 300 ppm of propadiene, 400 ppm of propyne, 2.0% n-butane, 6.0% isobutane, 19.0% n-butene, 28.3% isobutene, 5.5% trans-2-butene, 4.4% cis-2-butene, 39.0% 1,3-butadiene, 0.2% 1,2-butadiene, 1200 ppm of 1-butyne, 4500 ppm of vinylacetylene and 1000 ppm each of isopentane, 3-methyl-1-butene and 2-methyl-2-butene, based in each case on the total weight of the feed stream. $C_4$ oligomers and polymers may, according to storage and transport conditions, be present in the % range. In order to be usable as a feed stream in an extractive distillation, the above crude $C_4$ cut is subjected to a prepurification, for comparison in a plant with a distillation column in which the $C_3$ hydrocarbons are removed via the top and the other components are drawn off via the bottom, and then the bottom stream, for the purpose of removal of the high-boiling components compared to 1,3-butadiene, is supplied to a vaporizer vessel, i.e. an apparatus with a single plate. In the vaporizer vessel, the crude $C_4$ stream depleted of $C_3$ components is virtually completely evaporated, and discharged under flow rate control such that the high-boiling $C_5$ components compared to 1,3-butadiene in the remaining liquid component do not exceed 5% by weight, based on the total weight of crude $C_4$ cut supplied to the vaporizer vessel, in order to minimize the loss of $C_4$ components in the liquid residue. The proportion of the oligomers and polymers present in the liquid residue is much greater due to the lower vapor pressure. The liquid stream remaining in the vaporizer vessel is discharged as a purge stream.

According to the inventive example, the same crude $C_4$ cut is supplied as a feed stream to a vaporizer vessel VK, atop which is placed a stripping column K having 5 theoretical plates, to which the liquid $C_4$ cut 1 is supplied in the upper region thereof and from which the vaporous purified crude $C_4$ cut 2 is drawn off at the upper end thereof, the stripping column K being operated without a condenser at the top of the column. Such a plant is shown schematically in FIG. 1.

According to the prior art, less than 5% of the $C_5$ components present in the $C_4$ cut are removed via the residue stream (=purge stream), whereas, in the process according to the invention, more than one third of the $C_{5+}$ hydrocarbons present in the feed stream and more than 95% by weight of the $C_4$ oligomers and polymers present in the feed stream are discharged in the residue stream via the bottom.

The residue flow rate (from the vaporizer vessel) is, according to the prior art, 160 kg/h, with a proportion of 1,3-butadiene of 38.6% by weight.

Compared to this, the residue flow rate (bottoms flow rate) from the distillation column in the process according to the invention was likewise 160 kg/h, but with only 23% by weight of 1,3-butadiene. The yield of 1,3-butadiene in the predistillation (1,3-butadiene in the purified $C_4$ cut based on 1,3-butadiene in the crude $C_4$ cut) was, according to the prior art, 99.29% compared to 99.49% in the inventive example. This means that, in the process according to the invention, a higher yield of 1,3-butadiene product of value is achieved.

As a further advantage, in the process according to the invention, a purified crude $C_4$ cut is removed with higher purity compared to the prior art process. At 32 t/h of crude $C_4$ feed with a total of 3000% by weight ppm of $C_5$ components (there may additionally be further proportions of $C_6$ components and oligomers and polymers, which are not taken into account here), 94.16 kg/h of $C_5$ components are sent to the extractive distillation according to the prior art. In the inventive case, in contrast, only 55.1 kg/h of $C_5$ components are sent to the extractive distillation. Since a lower level of $C_5$ components from the predistillation is supplied to the extractive distillation, there is also a corresponding reduction in the loss of 1,3-butadiene in the extractive distillation or the subsequent purifying distillation. Based on the pure product (pure 1,3-butadiene) from the overall extractive distillation including predistillation, the yield of 1,3-butadiene (calculated as 100% 1,3-butadiene) according to the prior art is 96.47%, and in the inventive case 96.66%.

In an above-specified large-scale plant with 100 kt/a, the loss of 1,3-butadiene product of value is thus approx. 192 t/year greater in the process according to the prior art than in the process according to the invention.

By virtue of the fact that the solvent forms a closed circuit, the prior removal of troublesome components and impurities keeps the solvent clean, which minimizes regeneration complexity. At the same time, the fouling of the extractive distillation plant (fouling of the beds in the columns) and foam formation are minimized. As a result, less antifoam is required with correspondingly lower costs. Reduced fouling reduces the cleaning expenditure in the event of a shutdown. Every shutdown means a production outage of about 2 weeks; there is additional cleaning expenditure. This leads to costs in the 7-digit range.

The invention claimed is:

1. A process for providing a vaporous purified crude $C_4$ cut, the process comprising:
   removing $C_4$ oligomers and polymers and $C_{5+}$ hydrocarbons from a liquid crude $C_4$ cut feed stream, that comprises butanes, butenes, 1,3-butadiene, $C_3$ hydrocarbons, the $C_4$ oligomers and polymers, and the $C_{5+}$ hydrocarbons, thereby forming a purified liquid crude $C_4$ cut that comprises residual contents comprising less than two thirds of the $C_{5+}$ hydrocarbons and less than 5% by weight of the $C_4$ oligomers and polymers present in the feed stream, and
   vaporizing the purified liquid crude $C_4$ cut in a vaporizer vessel, thereby obtaining a vaporous purified crude $C_4$ cut
   wherein
   the vaporizer vessel is assigned a stripping column having one or more plates, to which the liquid crude $C_4$ cut feed stream is supplied in the upper region thereof, which is in direct gas and liquid exchange with the vaporizer vessel in the lower region thereof, and from which the vaporous purified crude $C_4$ cut is drawn off in the upper region thereof, the stripping column being operated without a condenser at the top of the column.

2. The process according to claim 1,
   wherein the stripping column is placed atop the vaporizer vessel.

3. The process according to claim 1,
   wherein the stripping column is associated with the vaporizer vessel as a separate apparatus.

4. The process according to claim 1,
   wherein the $C_3$ hydrocarbons are depleted in the vaporous purified crude $C_4$ cut to less than 10 ppm by weight, based on the total weight of the vaporous purified crude $C_4$ cut in a distillation column connected upstream of the vaporizer vessel.

5. The process according to claim 4,
   wherein the $C_3$ hydrocarbons are depleted to less than 4 ppm by weight, based on the total weight of the vaporous purified crude $C_4$ cut.

6. The process according to claim 1,
   wherein the $C_{5+}$ hydrocarbons are depleted to less than half of the $C_{5+}$ hydrocarbons present in the feed stream.

7. The process according to claim 1,
   wherein the stripping column is operated at a top pressure of from 3 to 7 bar absolute.

8. The process according to claim 7,
   wherein the stripping column is operated at a top pressure of from 4.5 to 5.5 bar absolute.

9. The process according to claim 1,
   wherein the stripping column has 1 to 15 theoretical plates.

* * * * *